US005511550A

United States Patent [19]

Finsterwald

[11] Patent Number: 5,511,550

[45] Date of Patent: Apr. 30, 1996

[54] ULTRASONIC TRANSDUCER ARRAY WITH APODIZED ELEVATION FOCUS

[75] Inventor: P. Michael Finsterwald, Scottsdale, Ariz.

[73] Assignee: Parallel Design, Inc., Tempe, Ariz.

[21] Appl. No.: 447,097

[22] Filed: May 22, 1995

Related U.S. Application Data

[63] Continuation of Ser. No. 324,104, Oct. 14, 1994, abandoned.

[51] Int. Cl.[6] .......... A61B 8/00

[52] U.S. Cl. .......... 128/662.03; 310/334

[58] Field of Search .......... 128/661.01, 662.03, 128/663.01; 310/334, 335, 336, 337, 357

[56] References Cited

U.S. PATENT DOCUMENTS

| | | | |
|---|---|---|---|
| 3,958,559 | 5/1976 | Glenn et al. | 128/2 V |
| 3,987,243 | 10/1976 | Schwartz | 178/6.8 |
| 4,217,684 | 8/1980 | Brisken | 29/25.35 |
| 4,250,474 | 2/1981 | Joseph | 333/196 |
| 4,333,065 | 6/1982 | DeVries | 333/194 |
| 4,425,525 | 1/1984 | Smith et al. | 310/336 |
| 4,452,084 | 6/1984 | Taenzer | 73/609 |
| 4,455,630 | 6/1984 | Loonen | 367/103 |
| 4,460,841 | 7/1984 | Smith et al. | 310/334 |
| 4,470,305 | 9/1984 | O'Donnell | 73/626 |
| 4,471,785 | 9/1984 | Wilson et al. | 128/660 |
| 4,518,889 | 5/1985 | Hoen | 310/357 |
| 4,550,607 | 11/1985 | Maslak et al. | 73/626 |
| 4,700,575 | 10/1987 | Geithman et al. | 73/642 |
| 4,784,147 | 11/1988 | Moshfeghi | 128/653 |
| 4,809,184 | 2/1989 | O'Donnell et al. | 364/413.25 |
| 4,815,047 | 3/1989 | Hart | 367/103 |
| 4,821,706 | 4/1989 | Schleicher et al. | 128/660.01 |
| 4,841,492 | 6/1989 | Russell | 367/105 |
| 4,890,268 | 12/1989 | Smith et al. | 367/138 |
| 4,917,097 | 4/1990 | Proudian et al. | 128/661.01 |
| 5,068,833 | 11/1991 | Lipschutz | 367/98 |
| 5,111,695 | 5/1992 | Engeler et al. | 73/626 |
| 5,119,342 | 6/1992 | Harrison, Jr. et al. | 367/7 |
| 5,140,558 | 8/1992 | Harrison, Jr. et al. | 367/7 |
| 5,187,981 | 2/1993 | Chen et al. | 73/642 |
| 5,235,986 | 8/1993 | Maslak et al. | 128/661.01 |
| 5,269,307 | 12/1993 | Fife et al. | 128/661.01 |
| 5,285,789 | 2/1994 | Chen et al. | 310/334 |

*Primary Examiner*—George Manuel
*Attorney, Agent, or Firm*—Pretty, Schroeder, Brueggemann & Clark; James R. Brueggemann

[57] ABSTRACT

An ultrasonic transducer array having a plurality of transducer elements aligned along an array axis in an imaging plane. Each transducer element includes a piezoelectric substrate and further includes a rear electrode applied to the substrate's rear surface and a patterned front electrode applied to the substrate's front surface. A conductive or metalized acoustic matching layer overlays the patterned front electrode. The front electrode is specially patterned along an elevation axis perpendicular to the imaging plane, so as to apodize the emitted ultrasonic beam in the elevation plane. The pattern follows a predetermined tapered weighting function, preferably one that approximates a Hamming weighting function. Slots, oriented parallel with the array axis, are cut into the piezoelectric substrate's front surface, to form a plurality of subelements. This further isolates these portions of the piezoelectric substrate not overlaid by the patterned front electrode, thereby enhancing beam apodization.

19 Claims, 14 Drawing Sheets

ULTRASONIC TRANSDUCER ARRAY WITH APODIZED ELEVATION FOCUS

This application is a continuation of application Ser. No. 08/324,104, filed Oct. 14, 1994, now abandoned.

BACKGROUND OF THE INVENTION

This invention relates generally to ultrasonic transducer arrays and, more particularly, to a linear or curvilinear array of acoustically isolated transducer elements having an apodized elevation focus.

In recent years, ultrasonic imaging techniques have become prevalent in clinical medical diagnoses and nondestructive testing of materials. In medical diagnostic imaging, these techniques have been used to measure and record the dimensions and positions of deeplying organs and physiological structures throughout the body.

Ultrasonic imaging systems typically include a plurality of parallel piezoelectric transducer elements arranged along an array axis, with each element having a piezoelectric layer and front and rear electrodes for exciting the piezoelectric layer and causing it to emit ultrasonic energy. An electronic driver circuit excites the transducer elements to form a thin beam of ultrasonic energy that can be scanned in the lateral direction, to define the imaging plane. The driver circuit can drive the plurality of piezoelectric elements in any of several conventional ways, to provide for example a phased array for sweeping a narrow beam along the imaging plane or a stepped array for step-wise directing a narrow beam in the imaging plane.

Beam forming in the elevation plane is more difficult because, for reasons of cost and simplicity, multiple transducer elements typically have not been provided along the elevational axis with which to electronically focus the beam. Often, an acoustic lens is placed in front of the transducer array, to provide a single elevation focus for the ultrasonic beam. However, diffraction, due to the finite length of the transducer crystal in the elevational direction, can cause side lobes to appear in elevation, which interfere with imaging by the main lobe. In addition, the depth of field of the focus produced by the lens can be unduly limited.

Apodization of the ultrasonic beam in the elevation axis has been attempted in the past, to reduce the magnitude of the beam's side lobes and thereby improve the transducer's resolution. In particular, a thin sheet of acoustic blocking material has been applied to selected portions of the front surfaces of piezoelectric transducer elements, to tailor the intensity of ultrasonic energy emitted at various positions along the front surfaces, generally reducing the intensity at the sides of the elements relative to their centers. However, using an acoustical blocking material is imprecise and requires the use of an additional layer.

Accordingly, there is a need for more efficient ultrasonic transducer array that provides an imaging beam having reduced elevational side lobes and relatively good focus over a wide depth of field, without requiring the use of acoustic blocking materials. The present invention satisfies this need.

SUMMARY OF THE INVENTION

The present invention is embodied in an ultrasonic transducer array having a patterned front electrode and conductive acoustic matching layer that provides an apodized imaging beam having reduced elevational side lobes. The apodization is accomplished by directly tailoring the ultrasonic energy emitted at various positions along the front surface of each transducer element. The ultrasonic transducer array also exhibits a relatively good focus over a wide depth of field.

More particularly, the ultrasonic transducer array includes a plurality of piezoelectric transducer elements aligned along an array axis in an imaging plane. Each piezoelectric transducer element includes a piezoelectric substrate with a front surface overlaid by a front electrode and further has a rear surface overlaid by a rear electrode. Electrical drive signals are applied to the front electrode via an overlaying first acoustic matching layer. The front electrode is patterned, to provide a predetermined tapered weighting function distributed along an elevation axis that is perpendicular to the imaging plane. This provides beam apodization in the elevation plane, with the beam's side lobes having a lower magnitude over that provided by a transducer element without apodization.

In a more detailed feature of the invention, the piezoelectric substrate of each transducer element has a series of slots cut into its front surface, oriented in a direction substantially parallel to the array axis. These slots form acoustically isolated subelements and further isolate those portions of the piezoelectric layer not overlaid by the front electrode, thus enhancing the desired beam apodization.

In another more detailed feature of the invention, the front electrode of each transducer element is specially patterned so that the element emits an ultrasonic beam having an energy distribution that approximates a Hamming weighting function. This is considered to provide a particularly desirable form of beam apodization.

The first acoustic matching layer may take either of two suitable forms. In one form, a thin metallic layer (e.g., copper) forms the first acoustic matching layer's rear surface, to conduct electrical signals to the patterned front electrode. Alternatively, the entire first acoustic matching layer may be formed of an electrically conductive material.

In another feature of the invention, each piezoelectric transducer element may include a second acoustic matching layer of uniform thickness, overlaying the first acoustic matching layer. Further, an acoustic lens of a dielectric material may overlay the acoustic matching layer(s). Finally, the front surface of each transducer element may have either a flat or a concave shape in the elevation plane.

Other features and advantages of the present invention should become apparent from the following description of the preferred embodiments, taken in conjunction with the accompanying drawings, which illustrate, by way of example, the principles of the invention.

The piezoelectric substrate has isolated front and rear electrodes.

Figure 4:
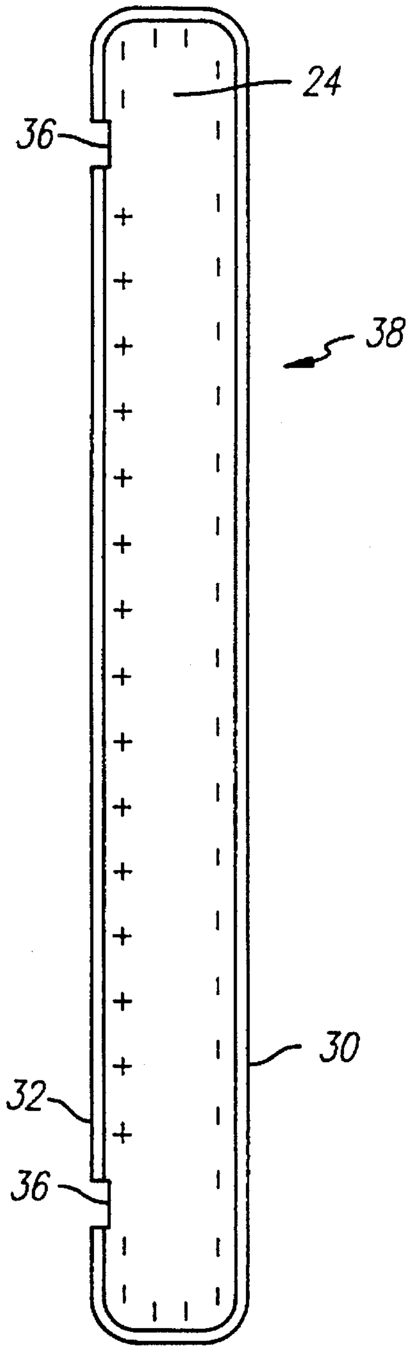
FIG. 4 is a cross-sectional view of a piezoelectric substrate, in an early stage of the manufacturing process, for use in the ultrasonic transducer array of the present invention.
Figure 5:
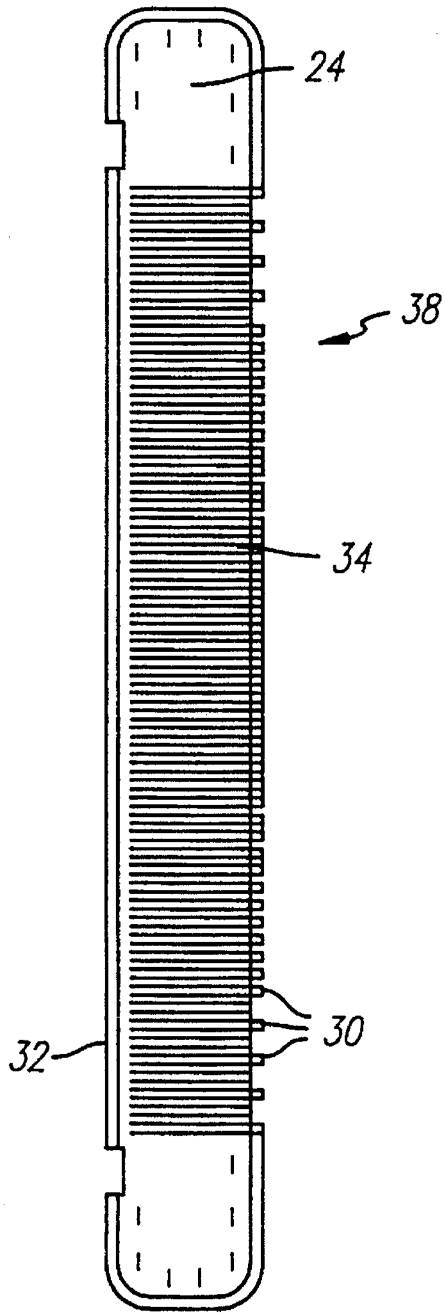

FIG. 5 is an end view of the piezoelectric substrate of FIG. 4, having a series of saw-cut slots and portions of the front electrode removed in a prescribed pattern.

Figure 6A:
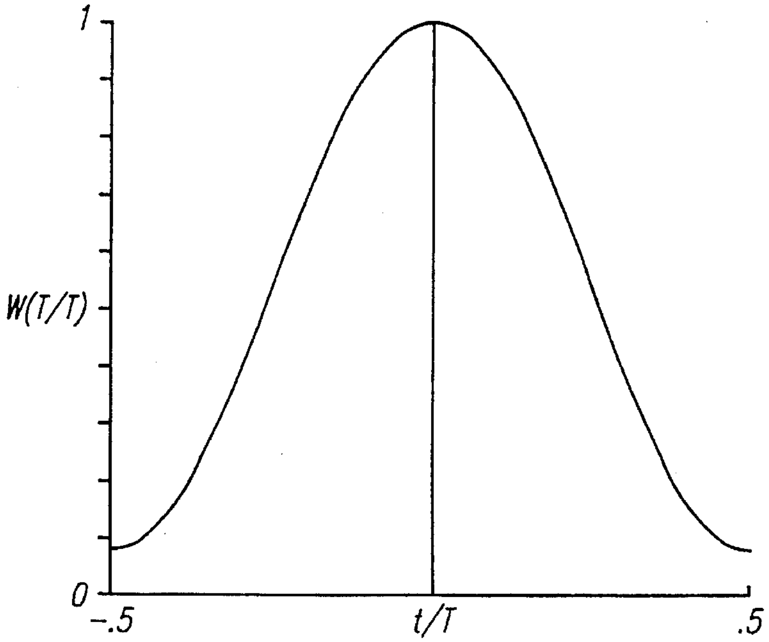
Figure 6B:
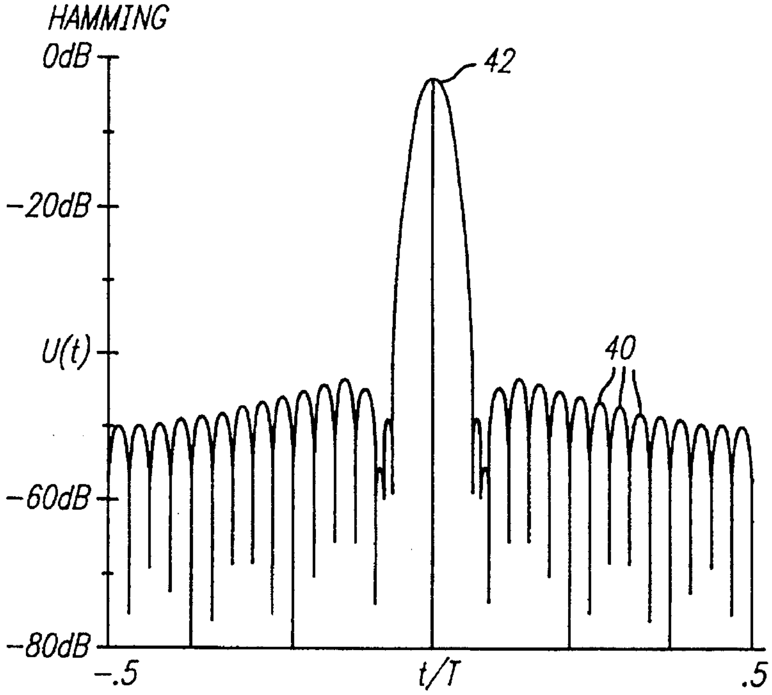

FIGS. 6A and 6B are graphs of a window weighted according to a Hamming weighting function and its associated Fourier transform, in log magnitude.

Figure 7A:
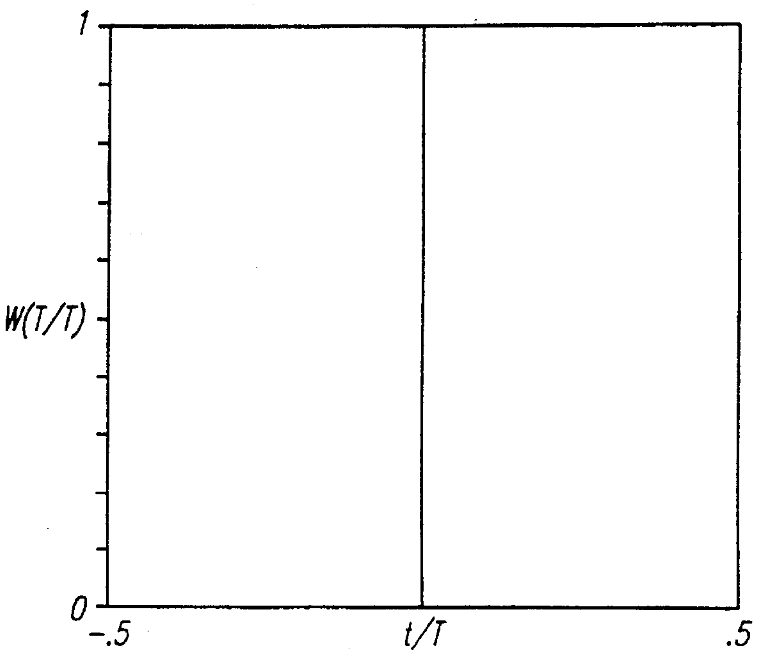
Figure 7B:
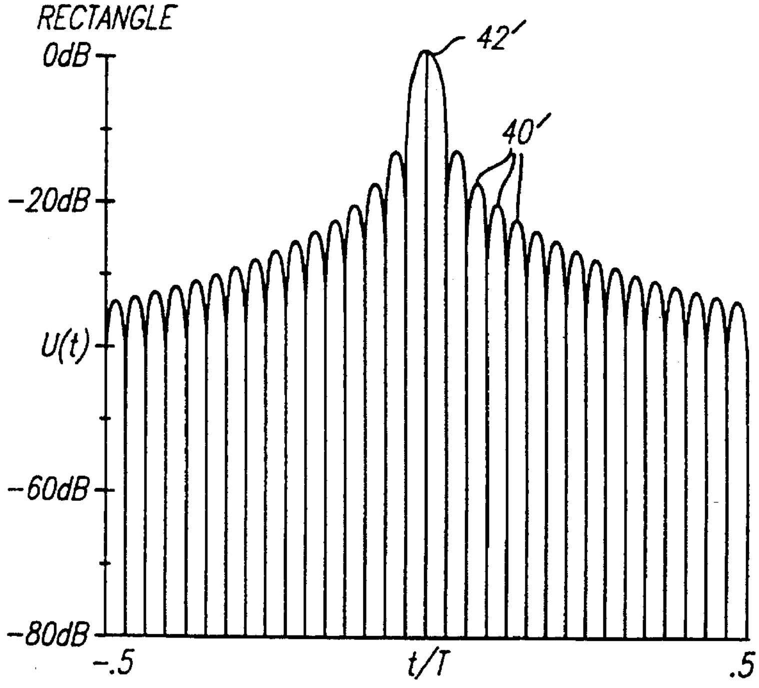

FIGS. 7A and 7B are graphs of a uniformly weighted rectangular window and its associated Fourier transform, in log magnitude.

Figure 8:
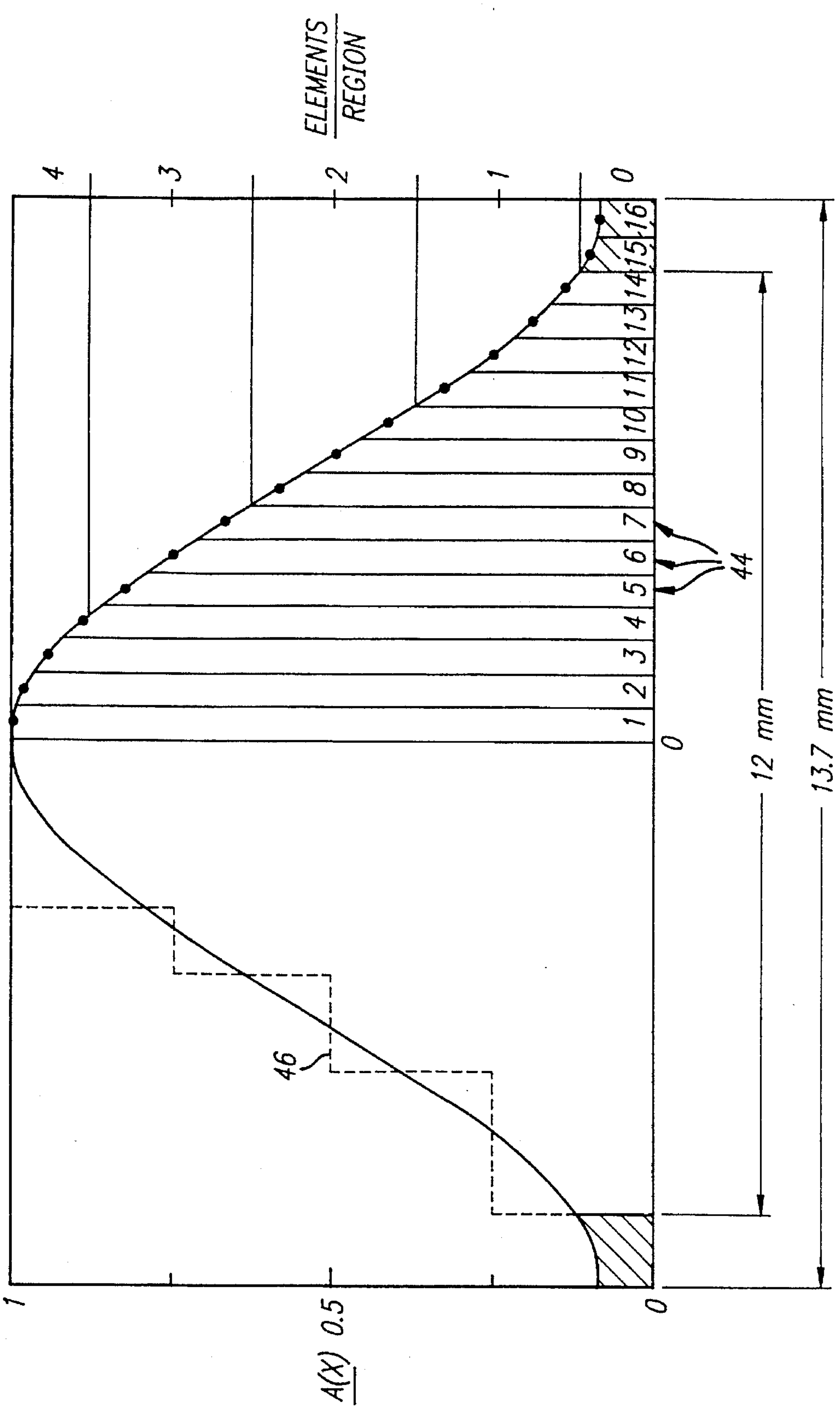

FIG. 8 is a graph of the Hamming weighting function of FIG. 6A divided into regions associated with portions of the front electrode of the ultrasonic transducer elements of the present invention.

Figure 9A:
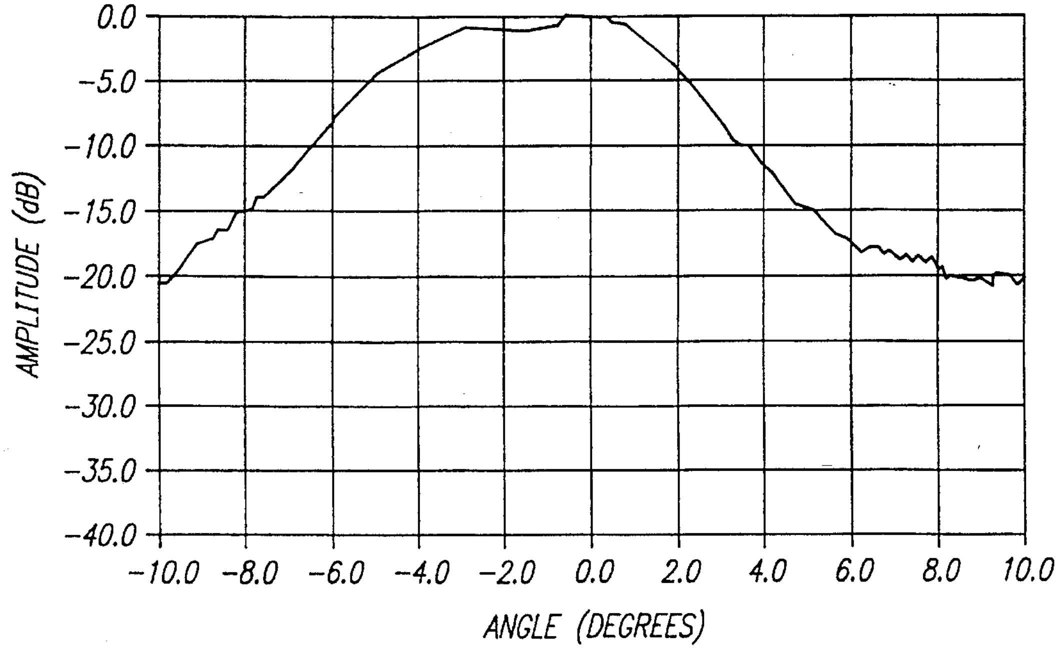

FIG. 9A is a graph of the elevation profile, at a distance of 40 millimeters from the transducer array, of a scanning beam produced by a transducer array having transducer elements that are uniformly weighted according to the graph in FIG. 7A.

Figure 9B:
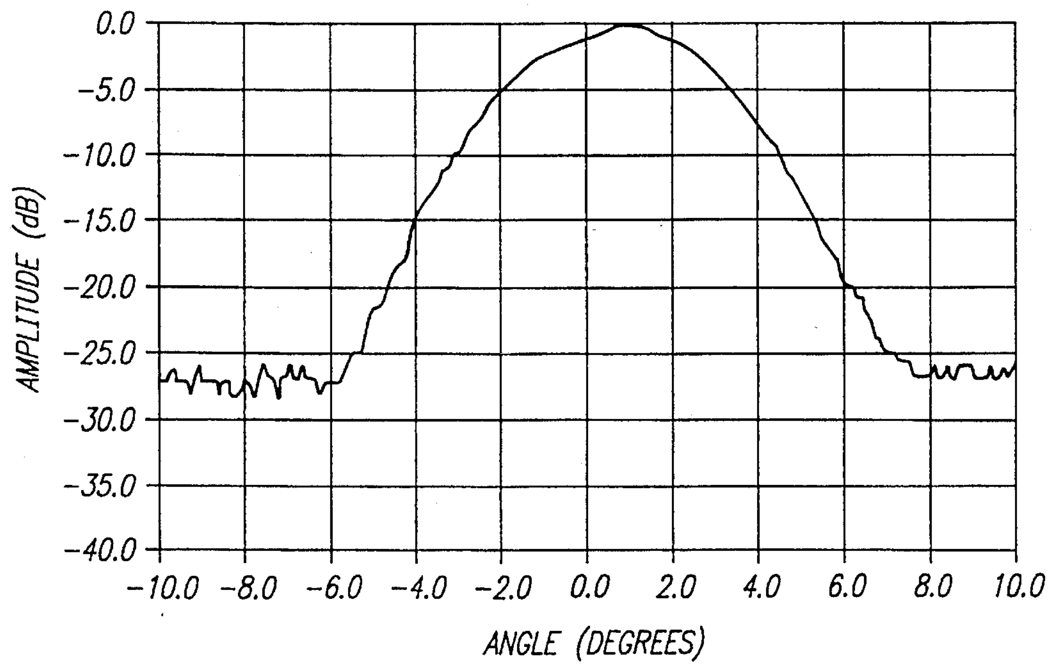

FIG. 9B is a graph of the elevation profile, at a distance of 40 millimeters from the transducer array, of a scanning beam produced by a transducer array having transducer elements that are weighted according to the Hamming weighting function of FIG. 8.

Figure 10A:
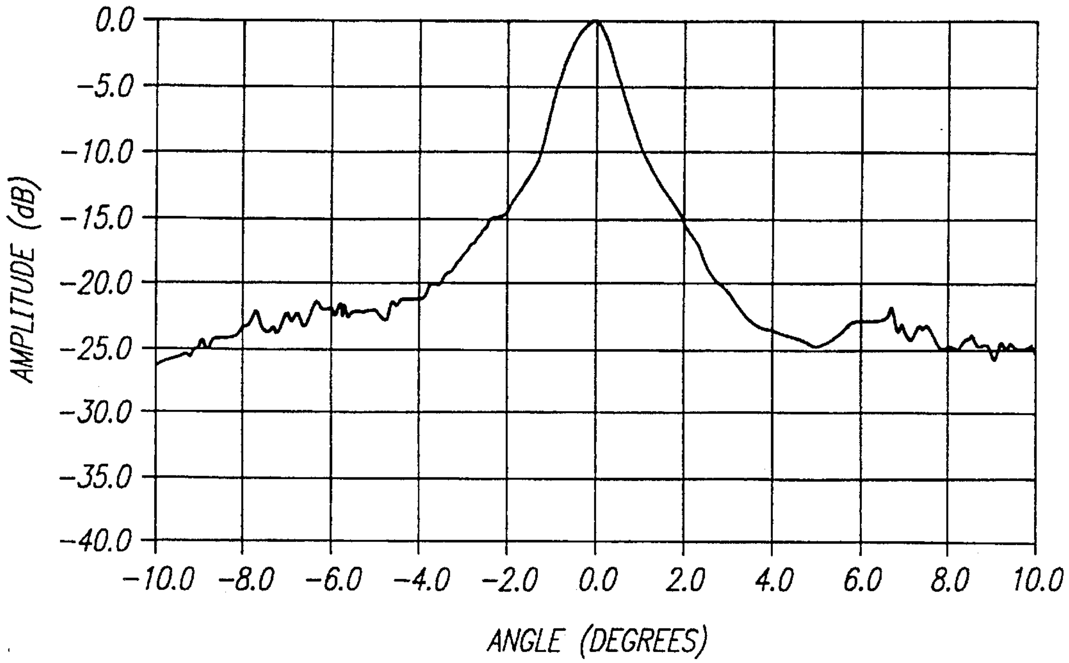

FIG. 10A is a graph of the elevation profile, at a distance of 60 millimeters from the transducer array, of a scanning beam produced by a transducer array having transducer elements that are uniformly weighted according to the graph in FIG. 7A.

Figure 10B:
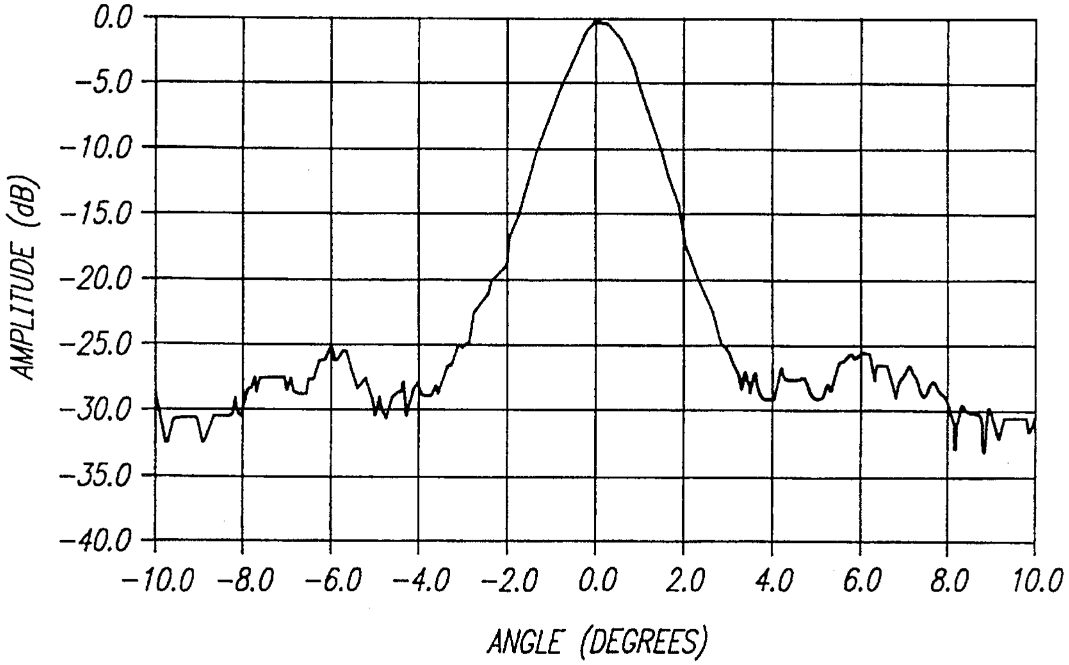

FIG. 10B is a graph of the elevation profile, at a distance of 60 millimeters from the transducer array, of a scanning beam produced by a transducer array having transducer elements that are weighted according to the Hamming weighting function of FIG. 8.

Figure 11A:
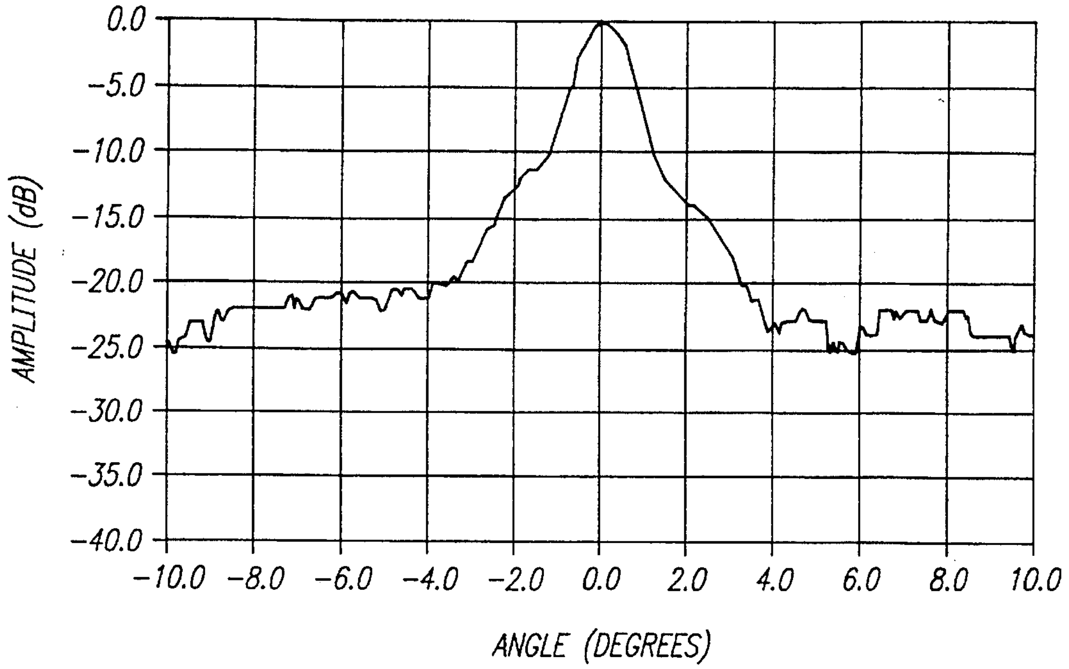

FIG. 11A is a graph of the elevation profile, at a distance of 80 millimeters from the transducer array, of a scanning beam produced by a transducer array having transducer elements that are uniformly weighted according to the graph in FIG. 7A.

Figure 11B:
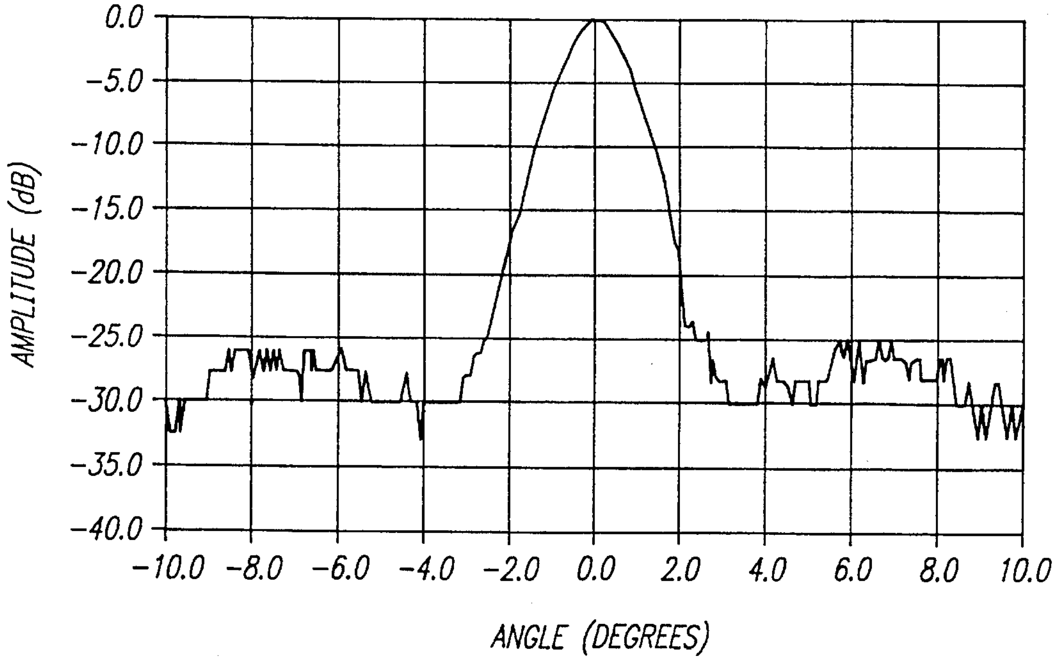

FIG. 11B is a graph of the elevation profile, at a distance of 80 millimeters from the transducer array, of a scanning beam produced by a transducer array having transducer elements that are weighted according to the Hamming weighting function of FIG. 8.

Figure 12A:
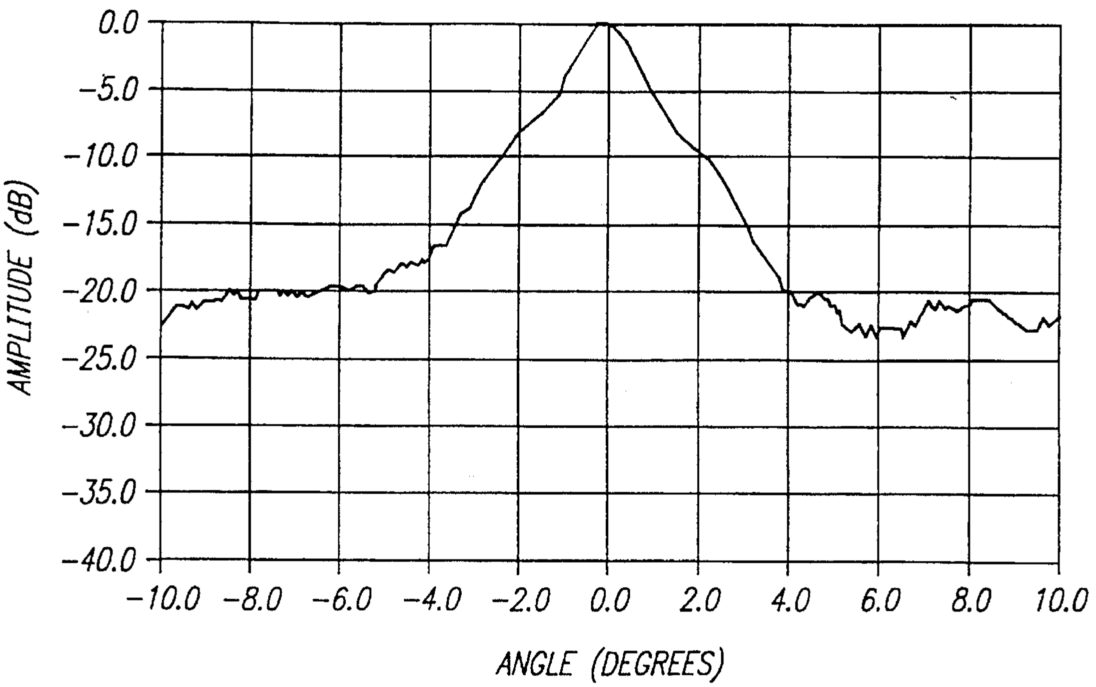

FIG. 12A is a graph of the elevation profile, at a distance of 100 millimeters from the transducer array, of a scanning beam produced by a transducer array having transducer elements that are uniformly weighted according to the graph in FIG. 7A.

Figure 12B:
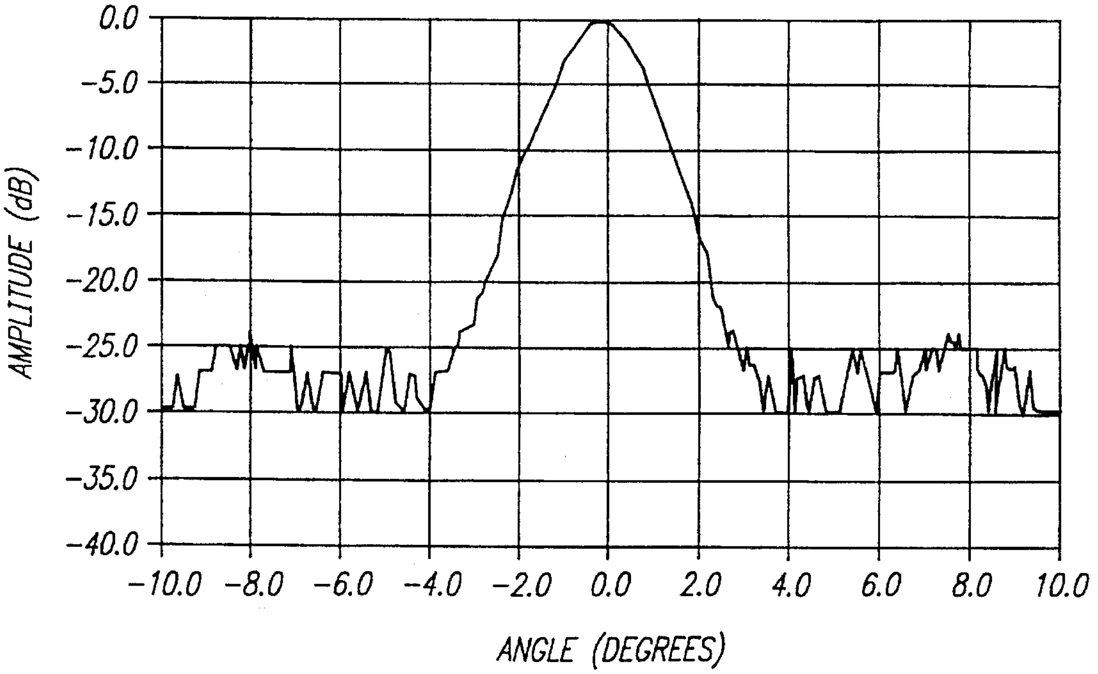

FIG. 12B is a graph of the elevation profile, at a distance of 100 millimeters from the transducer array, of a scanning beam produced by a transducer array having transducer elements that are weighted according to the Hamming weighting function of FIG. 8.

Figure 13A:
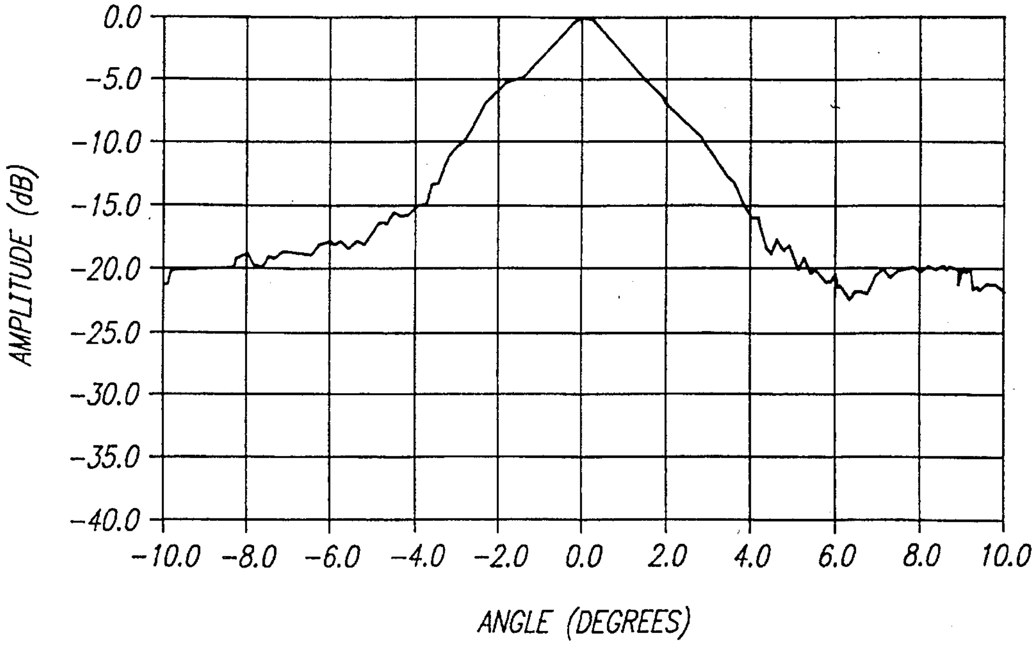

FIG. 13A is a graph of the elevation profile, at a distance of 120 millimeters from the transducer array, of a scanning beam produced by a transducer array having transducer elements that are uniformly weighted according to the graph in FIG. 7A.

Figure 13B:
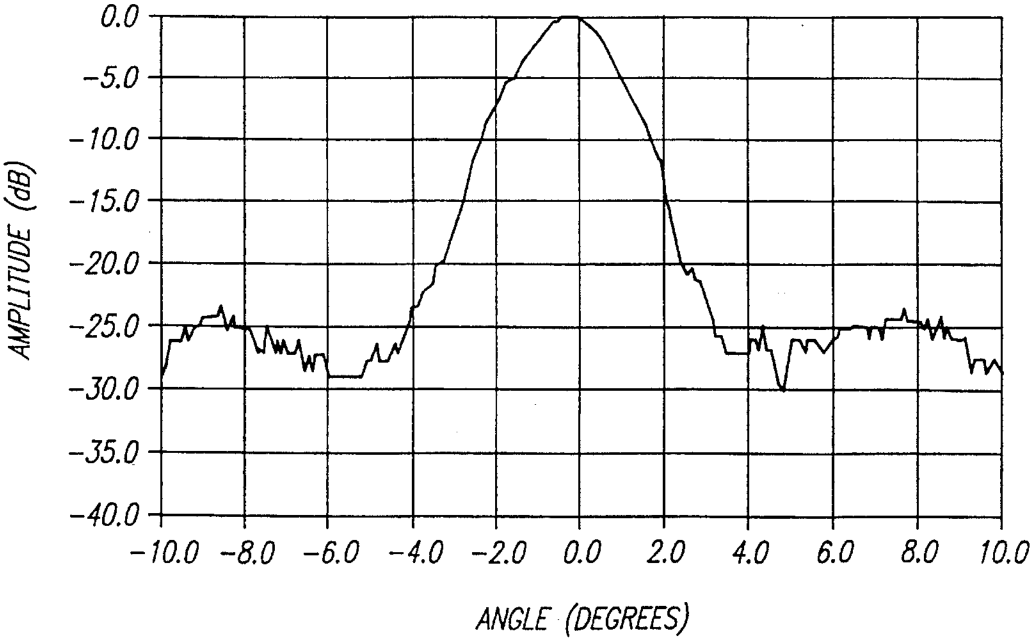

FIG. 13B is a graph of the elevation profile, at a distance of 120 millimeters from the transducer array, of a scanning beam produced by a transducer array having transducer elements that are weighted according to the Hamming weighting function of FIG. 8.

Figure 14:
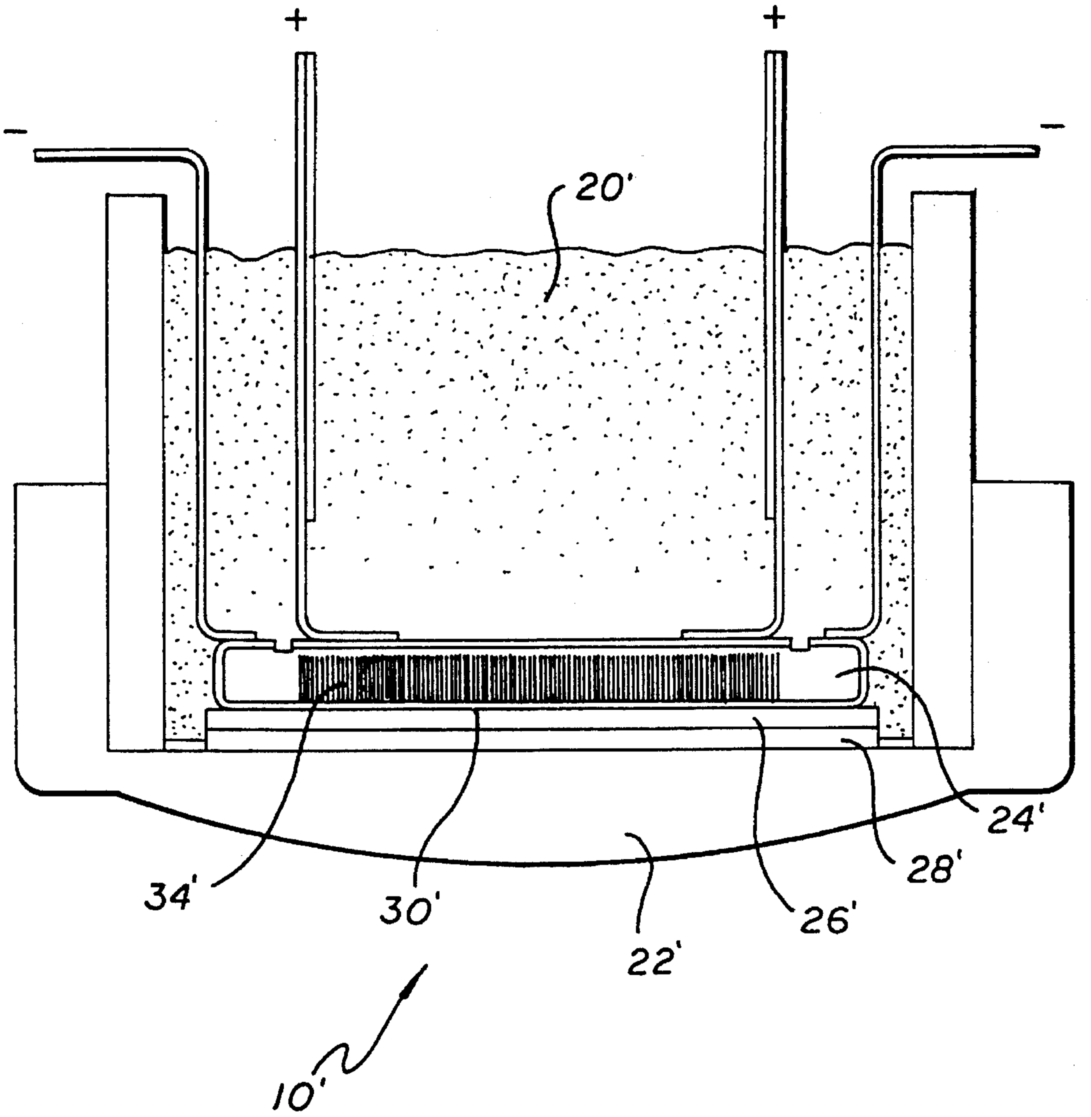

FIG. 14 is a cross-sectional side view of an alternative embodiment of the ultrasonic transducer array of the present invention.

Figure 15:
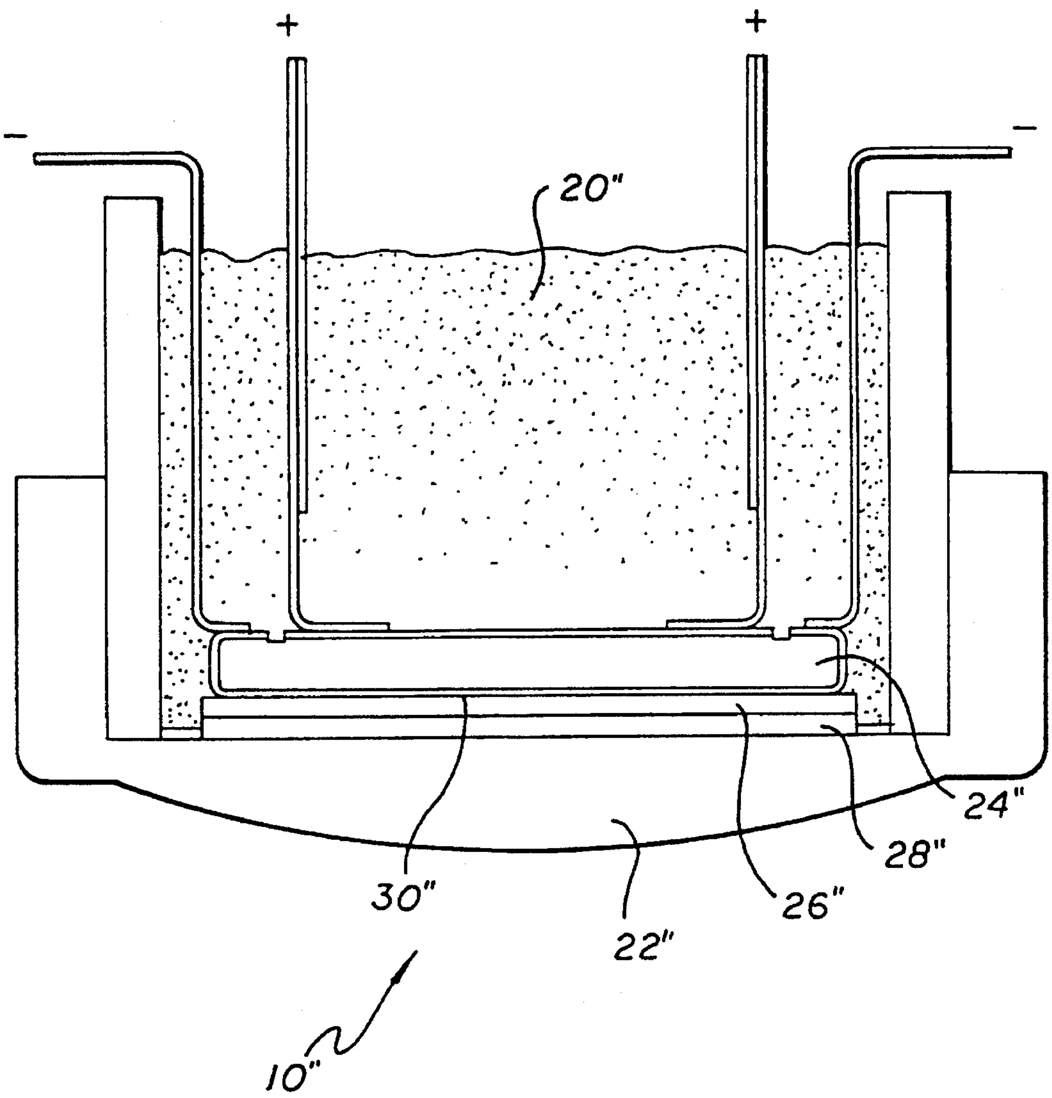

FIG. 15 is a cross-sectional view of another alternative embodiment of the ultrasonic transducer array of the present invention.

DESCRIPTION OF THE PREFERRED EMBODIMENTS

Figure 1:
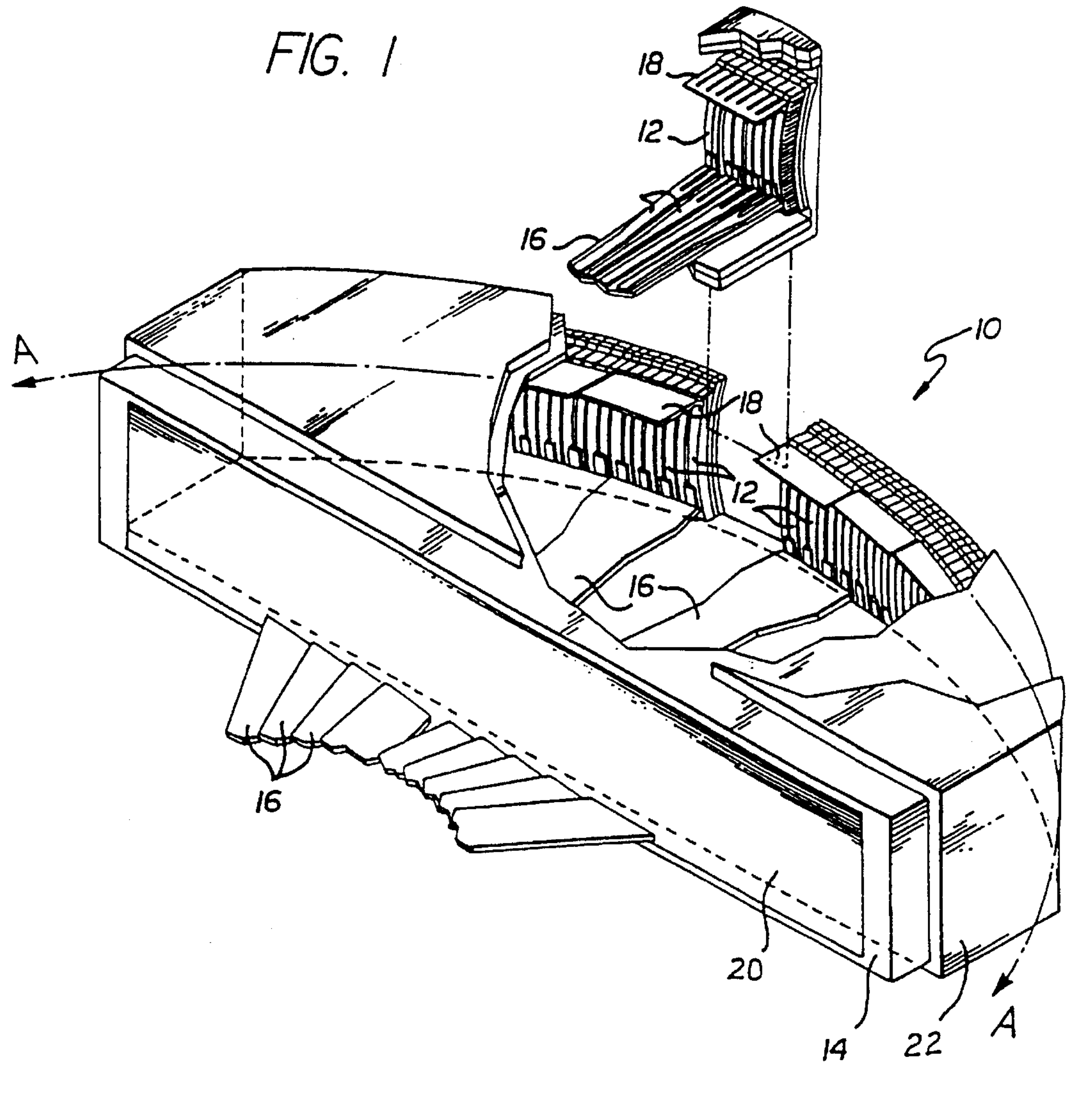
FIG. 1 is a perspective view, partly in section, of an ultrasonic transducer array of the present invention having a plurality of individual ultrasonic transducer elements. A portion of the array has been set out from the remainder, for illustrative purposes.
Figure 2:
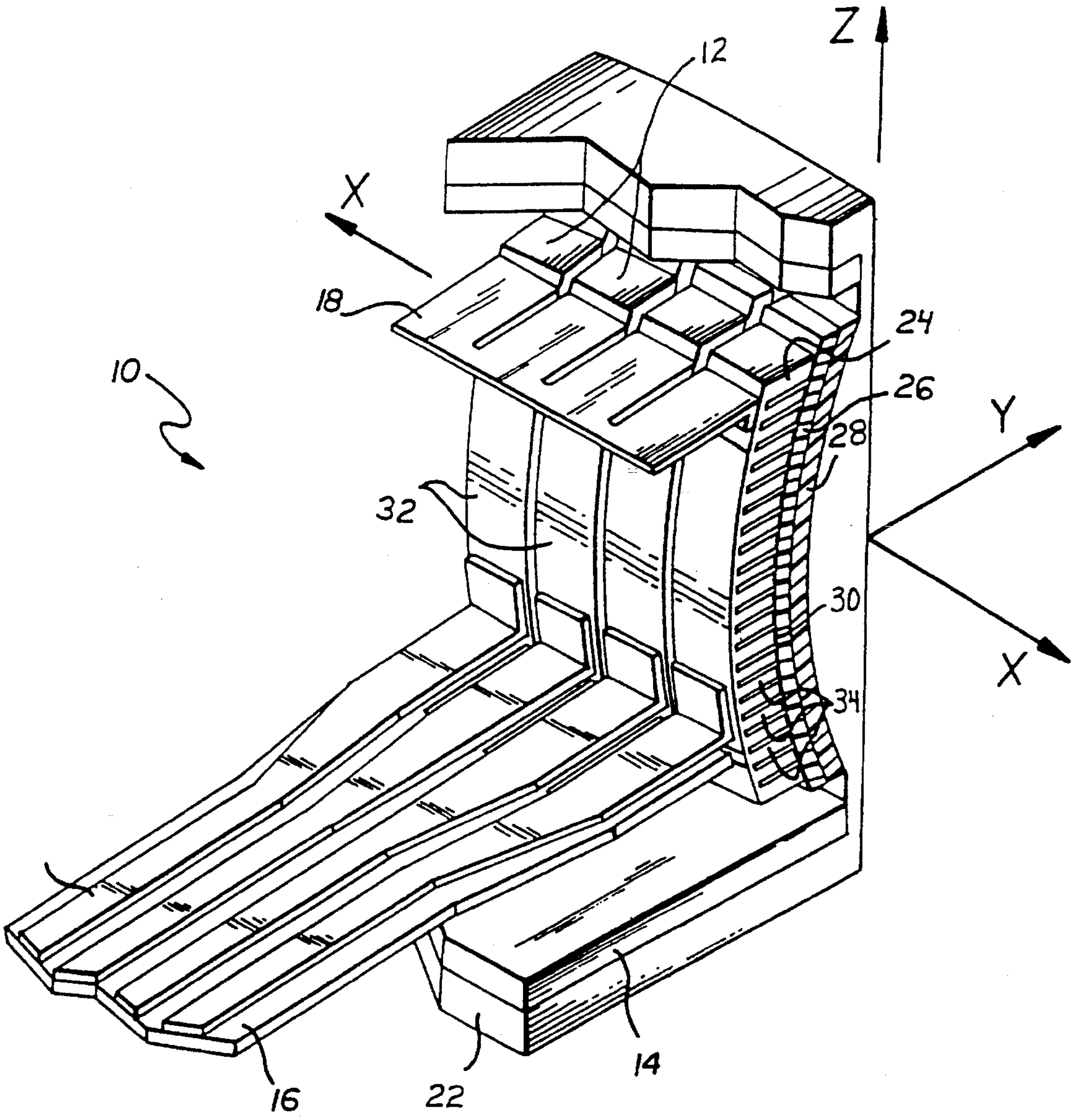
FIG. 2 is an enlarged sectional view of the set out portion of the array in FIG. 1, showing several of the ultrasonic transducer elements.
Figure 3:
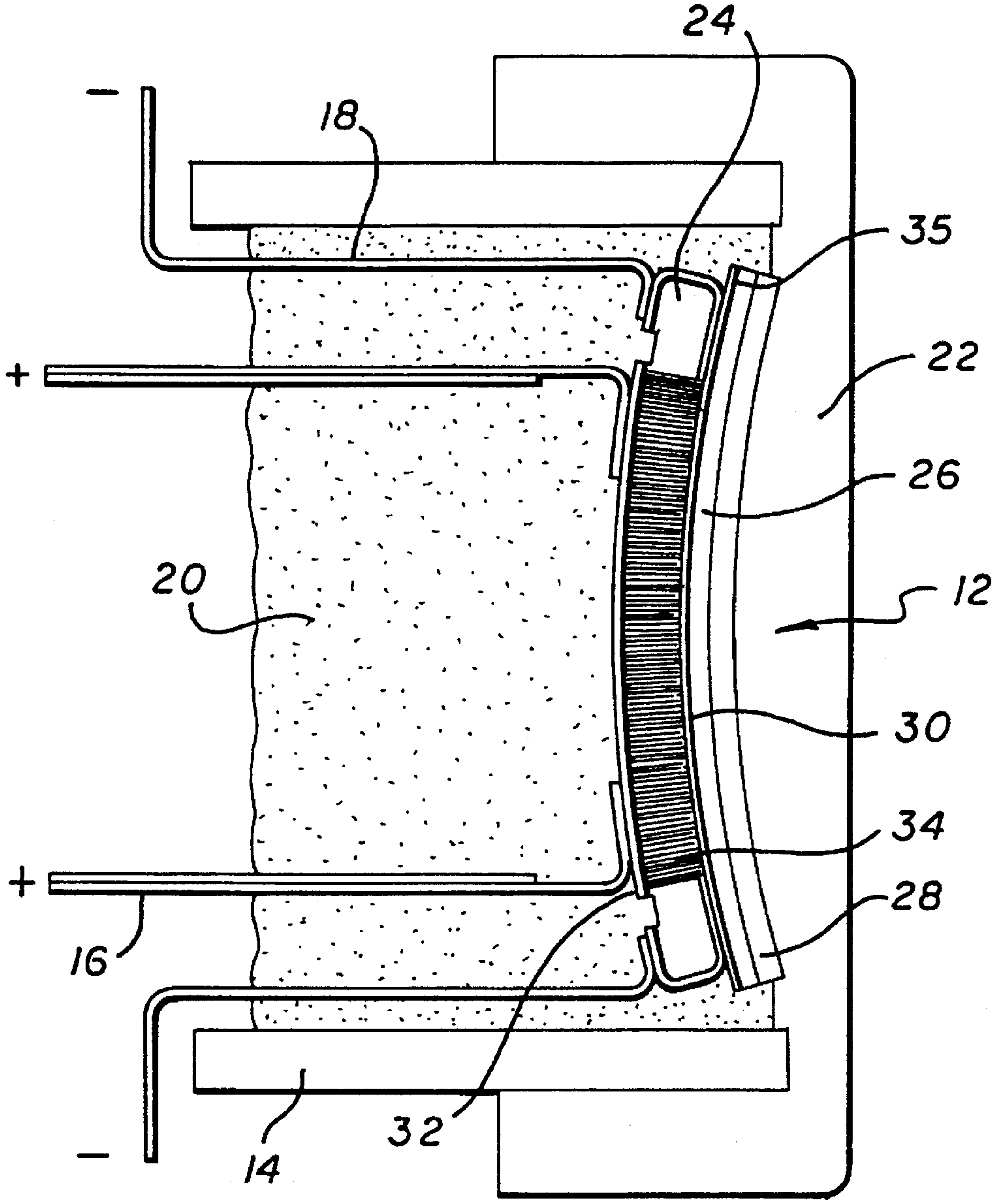
FIG. 3 is a cross-sectional side view of the ultrasonic transducer array of the present invention.

As shown in the exemplary drawings, and particularly in FIGS. 1–3, the present invention is embodied in an ultrasonic transducer array, generally referred to by the reference numeral 10, and a related method for imaging a target by scanning a narrow beam of ultrasonic energy in an imaging plane. The transducer array includes a plurality of acoustically isolated ultrasonic transducer elements 12 that are excited by signals of controlled amplitude and phase, causing the beam to scan in the imaging plane. The transducer array provides improved elevation focus of the beam due to apodization of the individual transducer elements by selectively exciting only selected portions of each element. This allows the transducer array to provide improved imaging.

The ultrasonic transducer array 10 includes a plurality of individual ultrasonic transducer elements 12 encased within a housing 14. The individual elements are electrically connected to the leads 16 of a flexible printed circuit board and to ground foils 18 that are fixed in position by a polymer backing material 20. A dielectric face layer 22 is formed around the transducer elements and the housing.

Each individual ultrasonic transducer element 12 includes a piezoelectric substrate 24, a first acoustic matching layer 26, and a second acoustic matching layer 28. The individual elements are mechanically isolated from each other and distributed along an array axis A located in an imaging plane, which is defined by the X-Y axes in FIG. 2. In addition, the individual elements are mechanically focused into the imaging plane, by forming the piezoelectric substrate and adjoining acoustic matching layers to have front surfaces that are concave.

The array axis A has a convex shape, to facilitate sector scanning. It will become apparent from the following description, however, that the array axis may be straight or curvilinear or may even have a combination of straight parts and curved parts. The ultrasonic transducer array can be formed and assembled by the method disclosed in U.S. patent application Ser. No. 08/010,827, filed Jan. 29, 1993, and entitled ULTRASONIC TRANSDUCER ARRAY AND MANUFACTURING METHOD THEREOF, which is incorporated herein by reference.

As shown in FIG. 3, each ultrasonic transducer element 12 of the present invention further includes a patterned front electrode 30 on the front surface of the piezoelectric substrate 24 and a rear electrode 32 on the substrate's rear surface. The patterned front electrode overlays a series of subelements 34 in the piezoelectric substrate. The rear electrode 32 is connected to a positive terminal via the lead 16, and the front, patterned electrode is connected to a negative terminal via the first acoustic matching layer 26 and the ground foils 18.

Preferably, the first acoustic matching layer is made of an epoxy material having a thickness equal to approximately one-quarter wavelength at the desired operating frequency (as measured by the speed of sound in the material). An electrically conductive layer 35 formed of a metal such as copper forms the rear surface of the first acoustic matching layer and provides the electrical conductivity to the patterned front electrode 30. Alternatively, an electrically conductive material possessing suitable acoustic impedance, such as graphite, silver-filled epoxy, or vitreous carbon, can be used for the first acoustic matching layer and the metallic layer can be omitted.

The second acoustic matching layer 28 has a uniform thickness and is sandwiched between the first acoustic matching layer 26 and the dielectric face layer 22. The second matching layer is preferred, but may be omitted.

Each transducer element 12 is excited by an excitation signal applied across the positive and negative terminals. The excitation signal causes those subelements 34 that are overlaid by the patterned front electrode 30 to vibrate, causing an ultrasonic wave to be emitted from the corresponding regions of the front surface of the piezoelectric substrate 24.

The piezoelectric transducer elements 12 are held within the housing 14 by the polymer-backing material 20. The dielectric face layer 22 is formed of a material such as polyurethane.

FIGS. 4 and 5 show the piezoelectric substrate 24 during preliminary stages of the manufacturing process, before the substrate has been formed into its concave shape. FIG. 4 shows the substrate after a metalization layer has been applied to its surfaces. Two saw cuts 36 through the metalization layer on the substrate's rear surface, form the front and rear electrodes 30 and 32, respectively. The saw cuts are placed to allow the front electrode 30 to wrap around to the substrate's back surface and thereby facilitate connection of the ground foils 18. An active aperture 38 on the front electrode is defined by the length of the rear electrode 32 projected onto the front electrode 30.

As shown in FIG. 5, the active aperture 38 of each transducer element 12 is divided into the subelements 34 by numerous parallel slots cut through the front surface of the piezoelectric substrate 24, parallel to the array axis A. The cuts are made using a dicing saw. As explained more fully in the above-referenced patent application, Ser. No. 08/010,827, the slots extend substantially through the piezoelectric substrate, which allows the substrate to flex and be formed into its concave shape. It will be noted that selected portions of the front electrode 30 are removed in the region of the active aperture. This selected removal is accomplished using a dicing saw, and it is performed so as to effect apodization, which is described below.

The elevation focus of the scanning beam generated by the transducer array 10 is improved by apodization of the transducer elements 12. Apodization of each transducer element is achieved by removing in elevation, i.e., in the direction of the Z-axis, portions of the front electrode 30, to provide a tapered excitation across the radiating aperture 38 of the piezoelectric substrate 24. Such electrode pattern is made on the front surface before the slots are cut.

Preferably, a Hamming weighting function, as shown in FIG. 6A, is used to apodize the beam. As shown in FIG. 6B, the Fourier transform of the Hamming weighting function has sides lobes 40 that are significantly below the level of the transform's main lobe 42. As compared with the rectangular weighting function and its Fourier transform, shown in FIGS. 7A and 7B, the side lobes 40 of the Hamming weighting function are much lower than the side lobes 40' of the rectangular weighting function, and the main lobe 42 is much wider than the main lobe 42' of the rectangular weighting function. Note that other weighting functions also may be used with some measure of success. In the environment of imaging within the body, which can contain many hard structures that produce large echoes, a slightly wider main lobe 42 is preferred over higher side lobes 40, which can induce significant noise caused by the hard structure echoes.

The Hamming weighting function at a cylindrical transducer has the form $$A(x)=0.08+0.92[\cos(\pi x/D)]^2$$

where:

x= distance from the central axis

D= total length of the aperture.

Note that the exact profile of the weighting function cannot be duplicated merely by removing portions of the front electrode 30. Therefore, the transducer elements 12 of the present invention approximate the weighting function by removing the front electrode from selected subelements 34 so that the selected subelements are not excited by the excitation signal for the respective transducer element. The subelements that should be removed from the front electrode are determined by dividing the subelements into groups or regions. The front electrode is removed from a select number of subelements in each group leaving the remaining elements in the group to emit ultrasonic energy. For a fixed number of subelements, the number of groups and the number of subelements in each group involves a tradeoff between having a sufficient number of groups to approximate the curve of the weighting function verses having a sufficient number of subelements in each group to minimize quantization effects.

In the preferred embodiment, the transducer elements 12 have an active elevation aperture 38 of 12 millimeters. The slots are evenly spaced across the elevation of the aperture to form 112 composite subelements 34. As shown in FIG. 8, each half of the aperture is divided into 14 regions 44 of four subelements each, for a total of 28 regions across the aperture. The number of subelements that should have the front electrode 30 removed in each region in order to approximate the Hamming weighting function can be calculated by determining the area under the curve of the weighting function corresponding to the regions of interest. It readily can be shown that for 14 regions of four subelements each, the last two regions should have the front electrode removed from all four subelements in each of these regions. However, it is unnecessary to have any regions within the active aperture 38 with no active subelements; the portion of the front surface of the piezoelectric substrate that extends past the rear electrode 32 on the piezoelectric substrate 24 effectively produces no ultrasonic energy can provide that function. Thus, for purposes of calculation, two phantom regions 15 and 16 are added at each end of the active aperture and the calculations performed for a transducer element having an effective active elevation aperture of 13.7 millimeters, with each half divided into 16 regions.

Since the Hamming weighting function is symmetrical about its center, the calculation is performed for only one-half of the 32 regions 44. The normalized area under the curve of the weighting function for each region in one-half of the curve is given by the formula:

$$Z_n=\frac{1}{D/32}\int_{(n-1)D/32}^{nD/32} A(x)dx$$

where:

n=1 to 16 (½ of the regions)

D=13.7 millimeters

The number of subelements $r_n$ that should have the electrode removed is calculated by the formula:

$$r_n=(Z_n-1)/4$$

Since there are only four elements per region 42, the number of subelements $r_n$ that should have the electrode removed is quantized to whole numbers or integers $i_n$ using predetermined thresholds. As a general guideline, a calculated number $r_n$ from: 0 to 0.5 indicates that no electrodes in the region should be removed, 0.5 to 1.5 indicates that one electrode should be removed from the region, 1.5 to 2.5 indicates that two electrodes should be removed from the region, 2.5 to 3.5 indicates that three electrodes should be removed from the region, and 3.5 to 4.0 indicates that four electrodes should be removed from the region.

Performing the calculations yields the following table:

| n | $Z_n$ | $r_n$ | $q_n$ | n | $Z_n$ | $r_n$ | $q_n$ |
|---|---|---|---|---|---|---|---|
| 1 | 0.996 | −0.015 | 0 | 9 | 0.389 | −2.443 | 2 |
| 2 | 0.973 | −0.107 | 0 | 10 | 0.297 | −2.813 | 2 |
| 3 | 0.929 | −0.285 | 0 | 11 | 0.216 | −3.135 | 3 |
| 4 | 0.865 | −0.541 | 0 | 12 | 0.152 | −3.392 | 3 |
| 5 | 0.785 | −0.861 | 0 | 13 | 0.107 | −3.571 | 3 |
| 6 | 0.692 | −1.231 | 1 | 14 | 0.084 | −3.664 | 3 |
| 7 | 0.592 | −1.632 | 1 | 15 | 0.084 | −3.665 | 4 |
| 8 | 0.489 | −2.042 | 2 | 16 | 0.106 | −3.575 | 4 |

Accordingly, in regions 1–4, no portion of the front electrode 30 should be removed from the subelements 34; in regions 5–7, the front electrode should be removed from one subelement; in regions 8–10, the front electrode should be removed from two subelements; in regions 11–14, the front electrode should be removed from three subelements; and finally, in regions 15 and 16, the front electrode should be removed from all four subelements, leaving no active subelements. As mentioned before, however, regions 15 and 16 are outside of the 12-millimeter active window or aperture 36 of the piezoelectric substrate 24 and correspond to the end portions of the piezoelectric substrate that do not emit any ultrasonic energy.

As shown in FIG. 8 by the dotted line 46 in the left half of the graph, the approximation of the Hamming weighting function is not extremely precise. The most important feature is that the distribution tapers off toward the ends of the aperture 38.

FIGS. 9A–13A show the elevation profile of a beam produced by a transducer array having a uniform elevation window at increasing distances from the array, and FIGS. 9B–13B show the elevation profile of a beam produced by a transducer array having an apodized elevation focus at increasing distances from the array. In the apodized transducer array, the active aperture 38 has 112 subelements 34 that are separated into 14 regions 44 of four subelements each. Regions 1–5 have four active subelements, regions 6 and 7 have three active subelements, regions 8–10 have two active subelements, and regions 11–14 have one active subelement. This arrangement thus differs from the more optimized arrangement discussed above only in the case of region number 5.

In the illustrated examples, at ranges of 20 millimeters and below, the beams are not well formed and there is little difference between the performance of the apodized beam and the uniform aperture beam. At a range of 40 millimeters, however, it can be seen that the apodized beam profile (FIG. 9B) has a more distinct main lobe 42 and at least a 5 dB improvement in signal rejection outside of the main lobe of the beam profile with no apodization (FIG. 9A). At ranges of 60 millimeters to 120 millimeters, the side lobes 40 for the apodized beam profiles (FIGS. 10B–13B) are at least approximately 5 dB lower than the beam profiles with no apodization (FIGS. 10A–13A). Accordingly, it will be appreciated that the ultrasonic transducer array 10 of the present invention significantly improves the imaging performance of the array by significantly lowering the level of the side lobes of the resulting ultrasonic beam.

An alternative embodiment of the transducer array 10' of the present invention is shown in FIG. 14. In this embodiment, the piezoelectric substrate 24' is flat, and the apodization is implemented on the front electrode 30' across the flat face of the piezoelectric substrate. Preferably, the dielectric face layer 22' forms a silicone rubber lens by having a curved outer surface, which focuses the ultrasonic beam in elevation.

Another alternative embodiment of the transducer array 10" of the present invention is shown in FIG. 15. In this embodiment, the slots that form the subelements 34 are eliminated. The front electrode 30" excites only those portions of the piezoelectric substrate 24" that are overlaid by the front electrode.

Although the foregoing discloses preferred embodiments of the present invention, it is understood that those skilled in the art may make various changes to the preferred embodiments shown without departing from the scope of the invention. The invention is defined only by the following claims.

I claim:

1. An ultrasonic transducer array for imaging a target, comprising a plurality of piezoelectric transducer elements aligned along an array axis in an imaging plane, each piezoelectric transducer element including:

a piezoelectric substrate having a front surface and a rear surface;

a patterned front electrode overlaying selected portions of the front surface of the piezoelectric substrate, such selected portions being less than the entire front surface;

a rear electrode overlaying the rear surface of the piezoelectric substrate; and a first acoustic matching layer overlaying the patterned front electrode and conducting electrical signals to the front electrode;

wherein the patterned front electrode is configured to provide a predetermined tapered weighting function distributed along an elevation axis, perpendicular to the imaging plane, thereby providing a beam of ultrasonic energy that is apodized in the elevation plane.

2. An ultrasonic transducer array as defined in claim 1, wherein the piezoelectric substrate of each transducer element has a series of slots cut into its front surface, the slots running in a direction substantially parallel to the array axis and forming acoustically isolated subelements.

3. An ultrasonic transducer array as defined in claim 2, wherein selected acoustically isolated subelements are coupled to the first acoustic matching layer by the patterned front electrode, so that the piezoelectric substrate emits an ultrasonic wave having a predetermined energy distribution.

4. An ultrasonic transducer array as defined in claim 1, wherein the predetermined tapered weighting function approximates a Hamming weighting function.

5. An ultrasonic transducer array as defined in claim 1, wherein the first acoustic matching layer includes an epoxy material layer and a metallic layer for conducting electrical signals.

6. An ultrasonic transducer array as defined in claim 1, wherein the first acoustic matching layer is made of an electrically conductive material.

7. An ultrasonic transducer array as defined in claim 1, wherein each transducer element is divided into subelements that are selectively overlaid by the patterned front electrode, such that the selected subelements are connected in parallel by the first acoustic matching layer.

8. An ultrasonic transducer array as defined in claim 1, wherein the front surface of the piezoelectric substrate of each transducer element has a concave shape in the elevation plane.

9. An ultrasonic transducer array as defined in claim 1, wherein the front surface of the piezoelectric substrate of each transducer element is substantially flat in the elevation plane.

10. An ultrasonic transducer array for imaging a target by scanning a narrow beam of ultrasonic energy in an imaging plane, the narrow beam having associated side lobes on both sides of a main lobe that extend in elevation away from the imaging plane, the transducer array comprising:

a plurality of transducer elements aligned along an array axis in the imaging plane, each of the plurality of transducer elements including a piezoelectric substrate having a front surface and a rear surface, a front electrode overlaying selected portions of the front surface of the piezoelectric substrate, such selected portions being less than the entire front surface, a rear electrode overlaying the rear surface of the piezoelectric substrate, and a first acoustic matching layer overlaying the front electrode and conducting electrical signals to the front electrode, wherein the front electrode is configured to approximate a predetermined weighting function, so that the transducer element produces an apodized beam of ultrasonic energy directed toward the target and focused in the elevation plane, with the beam's side lobes having a lower magnitude than the side lobes that would be emitted by a piezoelectric element having a uniform front electrode.

11. A method for ultrasonic imaging, comprising:

providing a plurality of piezoelectric transducer elements aligned along an array axis in an imaging plane, each piezoelectric transducer element including a piezoelectric substrate having a front surface and a rear surface, a patterned front electrode overlaying selected portions of the front surface of the piezoelectric substrate, such selected portions being less than the entire front surface and providing a predetermined tapered weighting function distributed along an elevation axis oriented perpendicular to the imaging plane, a rear electrode overlaying the rear surface of the piezoelectric substrate; and a first acoustic matching layer overlaying the front electrode and conducting electrical signals to the front electrode; and exciting each transducer element with an excitation signal applied between the rear electrode and the first acoustic matching layer, to cause those portions of the front surface of the piezoelectric substrate overlaid by the patterned front electrode to emit an ultrasonic beam toward a target, wherein the patterned front electrode is configured to provide an ultrasonic beam that is apodized in the elevation plane.

12. A method of ultrasonic imaging as defined in claim 11, wherein the piezoelectric substrate of each transducer element has a series of slots cut into its front surface, the slots oriented in a direction substantially parallel to the array axis and forming acoustically isolated subelements.

13. A method of ultrasonic imaging as defined in claim 12, wherein selected acoustically isolated subelements are coupled to the first acoustic layer by the patterned front electrode so that the piezoelectric substrate emits an ultrasonic beam having a predetermined energy distribution.

14. A method of ultrasonic imaging as defined in claim 11, wherein the first acoustic matching layer includes an epoxy material layer and a metallic layer for conducting electrical signals.

15. A method of ultrasonic imaging as defined in claim 11, wherein the first acoustic matching layer is made of an electrically conductive material.

16. A method of ultrasonic imaging as defined in claim 11, wherein each transducer element is divided into subelements that are selectively overlaid by the patterned front electrode, such that the selected subelements are connected in parallel by the first acoustic matching layer.

17. A method of ultrasonic imaging as defined in claim 11, wherein the front surface of the piezoelectric substrate of each transducer element has a concave shape in the elevation plane.

18. A method of ultrasonic imaging as defined in claim 11, wherein the front surface of the piezoelectric substrate of each transducer element is substantially flat in the elevation plane.

19. A method of ultrasonic imaging as defined in claim 11, wherein the predetermined weighing function approximates a Hamming weighting function.

* * * * *